(12) United States Patent
Todeschini (10) Patent No.: US 10,372,952 B2
(45) Date of Patent: *Aug. 6, 2019

(54) DEVICE HAVING LIGHT SOURCE TO REDUCE SURFACE PATHOGENS

(71) Applicant: Hand Held Products, Inc., Fort Mill, SC (US)

(72) Inventor: Erik Todeschini, Camillus, NY (US)

(73) Assignee: Hand Held Products, Inc., Fort Mill, SC (US)

( * ) Notice: Subject to any disclaimer, the term of this patent is extended or adjusted under 35 U.S.C. 154(b) by 223 days.

This patent is subject to a terminal disclaimer.

(21) Appl. No.: 15/426,558

(22) Filed: Feb. 7, 2017

(65) Prior Publication Data

US 2017/0147843 A1 May 25, 2017

Related U.S. Application Data

(63) Continuation of application No. 14/019,616, filed on Sep. 6, 2013, now Pat. No. 9,572,901.

(51) Int. Cl.
| | |
|---|---|
| *G06K 7/10* | (2006.01) |
| *A61L 2/10* | (2006.01) |
| *A61L 2/00* | (2006.01) |
| *G06K 7/14* | (2006.01) |
| *G06K 19/06* | (2006.01) |

(52) U.S. Cl.
CPC ........ *G06K 7/10564* (2013.01); *A61L 2/0047* (2013.01); *A61L 2/0052* (2013.01); *A61L 2/10* (2013.01); *G06K 7/10881* (2013.01); *G06K 7/1413* (2013.01); *G06K 19/06028* (2013.01); *A61L 2202/14* (2013.01); *A61L 2202/16* (2013.01)

(58) Field of Classification Search
CPC .............................. A61L 2/10; G06K 7/10564
USPC ........................................ 422/24; 250/455.11
See application file for complete search history.

(56) References Cited

U.S. PATENT DOCUMENTS

| | | | |
|---|---|---|---|
| 6,262,886 | B1 | 7/2001 | DiFonzo et al. |
| 6,832,725 | B2 | 12/2004 | Gardiner et al. |
| 7,128,266 | B2 | 10/2006 | Zhu et al. |
| 7,159,783 | B2 | 1/2007 | Walczyk et al. |
| 7,413,127 | B2 | 8/2008 | Ehrhart et al. |
| 7,726,575 | B2 | 6/2010 | Wang et al. |

(Continued)

FOREIGN PATENT DOCUMENTS

| | | |
|---|---|---|
| WO | 2013163789 A1 | 11/2013 |
| WO | 2013173985 A1 | 11/2013 |

(Continued)

OTHER PUBLICATIONS

U.S. Pat. Appl. No. 13/367,978, filed Feb. 7, 2012, (Feng et al.); now abandoned.

(Continued)

*Primary Examiner* — Kevin Joyner
(74) *Attorney, Agent, or Firm* — Additon, Higgins & Pendleton, P.A.

(57) ABSTRACT

A self-disinfecting device includes a housing with translucent material and an internal light source that is used to reduce surface pathogens on the translucent material. The device includes a processor and a light source positioned within the housing. At least a portion of the housing is translucent to radiation, and the light source emits radiation at a wavelength and an intensity that kills pathogens residing on the outer surface of the housing.

20 Claims, 3 Drawing Sheets

(56) References Cited

U.S. PATENT DOCUMENTS

| | | |
|---|---|---|
| 8,294,969 B2 | 10/2012 | Plesko |
| 8,317,105 B2 | 11/2012 | Kotlarsky et al. |
| 8,322,622 B2 | 12/2012 | Liu |
| 8,366,005 B2 | 2/2013 | Kotlarsky et al. |
| 8,371,507 B2 | 2/2013 | Haggerty et al. |
| 8,376,233 B2 | 2/2013 | Van Horn et al. |
| 8,381,979 B2 | 2/2013 | Franz |
| 8,390,909 B2 | 3/2013 | Plesko |
| 8,408,464 B2 | 4/2013 | Zhu et al. |
| 8,408,468 B2 | 4/2013 | Horn et al. |
| 8,408,469 B2 | 4/2013 | Good |
| 8,424,768 B2 | 4/2013 | Rueblinger et al. |
| 8,431,910 B1 | 4/2013 | Perry |
| 8,448,863 B2 | 5/2013 | Xian et al. |
| 8,457,013 B2 | 6/2013 | Essinger et al. |
| 8,459,557 B2 | 6/2013 | Havens et al. |
| 8,469,272 B2 | 6/2013 | Kearney |
| 8,474,712 B2 | 7/2013 | Kearney et al. |
| 8,479,992 B2 | 7/2013 | Kotlarsky et al. |
| 8,490,877 B2 | 7/2013 | Kearney |
| 8,517,271 B2 | 8/2013 | Kotlarsky et al. |
| 8,523,076 B2 | 9/2013 | Good |
| 8,528,818 B2 | 9/2013 | Ehrhart et al. |
| 8,544,737 B2 | 10/2013 | Gomez et al. |
| 8,548,420 B2 | 10/2013 | Grunow et al. |
| 8,550,335 B2 | 10/2013 | Samek et al. |
| 8,550,354 B2 | 10/2013 | Gannon et al. |
| 8,550,357 B2 | 10/2013 | Kearney |
| 8,556,174 B2 | 10/2013 | Kosecki et al. |
| 8,556,176 B2 | 10/2013 | Van Horn et al. |
| 8,556,177 B2 | 10/2013 | Hussey et al. |
| 8,559,767 B2 | 10/2013 | Barber et al. |
| 8,561,895 B2 | 10/2013 | Gomez et al. |
| 8,561,903 B2 | 10/2013 | Sauerwein |
| 8,561,905 B2 | 10/2013 | Edmonds et al. |
| 8,565,107 B2 | 10/2013 | Pease et al. |
| 8,571,307 B2 | 10/2013 | Li et al. |
| 8,579,200 B2 | 11/2013 | Samek et al. |
| 8,583,924 B2 | 11/2013 | Caballero et al. |
| 8,584,945 B2 | 11/2013 | Wang et al. |
| 8,587,595 B2 | 11/2013 | Wang |
| 8,587,697 B2 | 11/2013 | Hussey et al. |
| 8,588,869 B2 | 11/2013 | Sauerwein et al. |
| 8,590,789 B2 | 11/2013 | Nahill et al. |
| 8,596,539 B2 | 12/2013 | Havens et al. |
| 8,596,542 B2 | 12/2013 | Havens et al. |
| 8,596,543 B2 | 12/2013 | Havens et al. |
| 8,599,271 B2 | 12/2013 | Havens et al. |
| 8,599,957 B2 | 12/2013 | Peake et al. |
| 8,600,158 B2 | 12/2013 | Li et al. |
| 8,600,167 B2 | 12/2013 | Showering |
| 8,602,309 B2 | 12/2013 | Longacre et al. |
| 8,608,053 B2 | 12/2013 | Meier et al. |
| 8,608,071 B2 | 12/2013 | Liu et al. |
| 8,611,309 B2 | 12/2013 | Wang et al. |
| 8,615,487 B2 | 12/2013 | Gomez et al. |
| 8,621,123 B2 | 12/2013 | Caballero |
| 8,622,303 B2 | 1/2014 | Meier et al. |
| 8,628,013 B2 | 1/2014 | Ding |
| 8,628,015 B2 | 1/2014 | Wang et al. |
| 8,628,016 B2 | 1/2014 | Winegar |
| 8,629,926 B2 | 1/2014 | Wang |
| 8,630,491 B2 | 1/2014 | Longacre et al. |
| 8,635,309 B2 | 1/2014 | Berthiaume et al. |
| 8,636,200 B2 | 1/2014 | Kearney |
| 8,636,212 B2 | 1/2014 | Nahill et al. |
| 8,636,215 B2 | 1/2014 | Ding et al. |
| 8,636,224 B2 | 1/2014 | Wang |
| 8,638,806 B2 | 1/2014 | Wang et al. |
| 8,640,958 B2 | 2/2014 | Lu et al. |
| 8,640,960 B2 | 2/2014 | Wang et al. |
| 8,643,717 B2 | 2/2014 | Li et al. |
| 8,646,692 B2 | 2/2014 | Meier et al. |
| 8,646,694 B2 | 2/2014 | Wang et al. |
| 8,657,200 B2 | 2/2014 | Ren et al. |
| 8,659,397 B2 | 2/2014 | Vargo et al. |
| 8,668,149 B2 | 3/2014 | Good |
| 8,678,285 B2 | 3/2014 | Kearney |
| 8,678,286 B2 | 3/2014 | Smith et al. |
| 8,682,077 B1 | 3/2014 | Longacre |
| D702,237 S | 4/2014 | Oberpriller et al. |
| 8,687,282 B2 | 4/2014 | Feng et al. |
| 8,692,927 B2 | 4/2014 | Pease et al. |
| 8,695,880 B2 | 4/2014 | Bremer et al. |
| 8,698,949 B2 | 4/2014 | Grunow et al. |
| 8,702,000 B2 | 4/2014 | Barber et al. |
| 8,717,494 B2 | 5/2014 | Gannon |
| 8,720,783 B2 | 5/2014 | Biss et al. |
| 8,723,804 B2 | 5/2014 | Fletcher et al. |
| 8,723,904 B2 | 5/2014 | Marty et al. |
| 8,727,223 B2 | 5/2014 | Wang |
| 8,740,082 B2 | 6/2014 | Wilz |
| 8,740,085 B2 | 6/2014 | Furlong et al. |
| 8,746,563 B2 | 6/2014 | Hennick et al. |
| 8,750,445 B2 | 6/2014 | Peake et al. |
| 8,752,766 B2 | 6/2014 | Xian et al. |
| 8,756,059 B2 | 6/2014 | Braho et al. |
| 8,757,495 B2 | 6/2014 | Qu et al. |
| 8,760,563 B2 | 6/2014 | Koziol et al. |
| 8,763,909 B2 | 7/2014 | Reed et al. |
| 8,777,108 B2 | 7/2014 | Coyle |
| 8,777,109 B2 | 7/2014 | Oberpriller et al. |
| 8,779,898 B2 | 7/2014 | Havens et al. |
| 8,781,520 B2 | 7/2014 | Payne et al. |
| 8,783,573 B2 | 7/2014 | Havens et al. |
| 8,789,757 B2 | 7/2014 | Barten |
| 8,789,758 B2 | 7/2014 | Hawley et al. |
| 8,789,759 B2 | 7/2014 | Xian et al. |
| 8,794,520 B2 | 8/2014 | Wang et al. |
| 8,794,522 B2 | 8/2014 | Ehrhart |
| 8,794,525 B2 | 8/2014 | Amundsen et al. |
| 8,794,526 B2 | 8/2014 | Wang et al. |
| 8,798,367 B2 | 8/2014 | Ellis |
| 8,807,431 B2 | 8/2014 | Wang et al. |
| 8,807,432 B2 | 8/2014 | Van Horn et al. |
| 8,820,630 B2 | 9/2014 | Qu et al. |
| 8,822,848 B2 | 9/2014 | Meagher |
| 8,824,692 B2 | 9/2014 | Sheerin et al. |
| 8,824,696 B2 | 9/2014 | Braho |
| 8,842,849 B2 | 9/2014 | Wahl et al. |
| 8,844,822 B2 | 9/2014 | Kotlarsky et al. |
| 8,844,823 B2 | 9/2014 | Fritz et al. |
| 8,849,019 B2 | 9/2014 | Li et al. |
| D716,285 S | 10/2014 | Chaney et al. |
| 8,851,383 B2 | 10/2014 | Yeakley et al. |
| 8,854,633 B2 | 10/2014 | Laffargue |
| 8,866,963 B2 | 10/2014 | Grunow et al. |
| 8,868,421 B2 | 10/2014 | Braho et al. |
| 8,868,519 B2 | 10/2014 | Maloy et al. |
| 8,868,802 B2 | 10/2014 | Barten |
| 8,868,803 B2 | 10/2014 | Caballero |
| 8,870,074 B1 | 10/2014 | Gannon |
| 8,879,639 B2 | 11/2014 | Sauerwein |
| 8,880,426 B2 | 11/2014 | Smith |
| 8,881,983 B2 | 11/2014 | Havens et al. |
| 8,881,987 B2 | 11/2014 | Wang |
| 8,903,172 B2 | 12/2014 | Smith |
| 8,908,995 B2 | 12/2014 | Benos et al. |
| 8,910,870 B2 | 12/2014 | Li et al. |
| 8,910,875 B2 | 12/2014 | Ren et al. |
| 8,914,290 B2 | 12/2014 | Hendrickson et al. |
| 8,914,788 B2 | 12/2014 | Pettinelli et al. |
| 8,915,439 B2 | 12/2014 | Feng et al. |
| 8,915,444 B2 | 12/2014 | Havens et al. |
| 8,916,789 B2 | 12/2014 | Woodburn |
| 8,918,250 B2 | 12/2014 | Hollifield |
| 8,918,564 B2 | 12/2014 | Caballero |
| 8,925,818 B2 | 1/2015 | Kosecki et al. |
| 8,939,374 B2 | 1/2015 | Jovanovski et al. |
| 8,942,480 B2 | 1/2015 | Ellis |
| 8,944,313 B2 | 2/2015 | Williams et al. |
| 8,944,327 B2 | 2/2015 | Meier et al. |
| 8,944,332 B2 | 2/2015 | Harding et al. |
| 8,950,678 B2 | 2/2015 | Germaine et al. |

(56) References Cited

U.S. PATENT DOCUMENTS

| | | |
|---|---|---|
| D723,560 S | 3/2015 | Zhou et al. |
| 8,967,468 B2 | 3/2015 | Gomez et al. |
| 8,971,346 B2 | 3/2015 | Sevier |
| 8,976,030 B2 | 3/2015 | Cunningham et al. |
| 8,976,368 B2 | 3/2015 | Akel et al. |
| 8,978,981 B2 | 3/2015 | Guan |
| 8,978,983 B2 | 3/2015 | Bremer et al. |
| 8,978,984 B2 | 3/2015 | Hennick et al. |
| 8,985,456 B2 | 3/2015 | Zhu et al. |
| 8,985,457 B2 | 3/2015 | Soule et al. |
| 8,985,459 B2 | 3/2015 | Kearney et al. |
| 8,985,461 B2 | 3/2015 | Gelay et al. |
| 8,988,578 B2 | 3/2015 | Showering |
| 8,988,590 B2 | 3/2015 | Gillet et al. |
| 8,991,704 B2 | 3/2015 | Hopper et al. |
| 8,996,194 B2 | 3/2015 | Davis et al. |
| 8,996,384 B2 | 3/2015 | Funyak et al. |
| 8,998,091 B2 | 4/2015 | Edmonds et al. |
| 9,002,641 B2 | 4/2015 | Showering |
| 9,007,368 B2 | 4/2015 | Laffargue et al. |
| 9,010,641 B2 | 4/2015 | Qu et al. |
| 9,015,513 B2 | 4/2015 | Murawski et al. |
| 9,016,576 B2 | 4/2015 | Brady et al. |
| D730,357 S | 5/2015 | Fitch et al. |
| 9,022,288 B2 | 5/2015 | Nahill et al. |
| 9,030,964 B2 | 5/2015 | Essinger et al. |
| 9,033,240 B2 | 5/2015 | Smith et al. |
| 9,033,242 B2 | 5/2015 | Gillet et al. |
| 9,036,054 B2 | 5/2015 | Koziol et al. |
| 9,037,344 B2 | 5/2015 | Chamberlin |
| 9,038,911 B2 | 5/2015 | Xian et al. |
| 9,038,915 B2 | 5/2015 | Smith |
| D730,901 S | 6/2015 | Oberpriller et al. |
| D730,902 S | 6/2015 | Fitch et al. |
| D733,112 S | 6/2015 | Chaney et al. |
| 9,047,098 B2 | 6/2015 | Barten |
| 9,047,359 B2 | 6/2015 | Caballero et al. |
| 9,047,420 B2 | 6/2015 | Caballero |
| 9,047,525 B2 | 6/2015 | Barber |
| 9,047,531 B2 | 6/2015 | Showering et al. |
| 9,049,640 B2 | 6/2015 | Wang et al. |
| 9,053,055 B2 | 6/2015 | Caballero |
| 9,053,378 B1 | 6/2015 | Hou et al. |
| 9,053,380 B2 | 6/2015 | Xian et al. |
| 9,057,641 B2 | 6/2015 | Amundsen et al. |
| 9,058,526 B2 | 6/2015 | Powilleit |
| 9,064,165 B2 | 6/2015 | Havens et al. |
| 9,064,167 B2 | 6/2015 | Xian et al. |
| 9,064,168 B2 | 6/2015 | Todeschini et al. |
| 9,064,254 B2 | 6/2015 | Todeschini et al. |
| 9,066,032 B2 | 6/2015 | Wang |
| 9,070,032 B2 | 6/2015 | Corcoran |
| D734,339 S | 7/2015 | Zhou et al. |
| D734,751 S | 7/2015 | Oberpriller et al. |
| 9,082,023 B2 | 7/2015 | Feng et al. |
| 9,224,022 B2 | 12/2015 | Ackley et al. |
| 9,224,027 B2 | 12/2015 | Van Horn et al. |
| D747,321 S | 1/2016 | London et al. |
| 9,230,140 B1 | 1/2016 | Ackley |
| 9,443,123 B2 | 1/2016 | Hejl |
| 9,250,712 B1 | 2/2016 | Todeschini |
| 9,258,033 B2 | 2/2016 | Showering |
| 9,262,633 B1 | 2/2016 | Todeschini et al. |
| 9,310,609 B2 | 4/2016 | Rueblinger et al. |
| D757,009 S | 5/2016 | Oberpriller et al. |
| 9,342,724 B2 | 5/2016 | McCloskey |
| 9,375,945 B1 | 6/2016 | Bowles |
| D760,719 S | 7/2016 | Zhou et al. |
| 9,390,596 B1 | 7/2016 | Todeschini |
| D762,604 S | 8/2016 | Fitch et al. |
| D762,647 S | 8/2016 | Fitch et al. |
| 9,412,242 B2 | 8/2016 | Van Horn et al. |
| D766,244 S | 9/2016 | Zhou et al. |
| 9,443,222 B2 | 9/2016 | Singel et al. |
| 9,478,113 B2 | 10/2016 | Xie et al. |
| 9,572,901 B2 | 2/2017 | Todeschini |
| 2007/0063048 A1 | 3/2007 | Havens et al. |
| 2009/0134221 A1 | 5/2009 | Zhu et al. |
| 2009/0200378 A1 | 8/2009 | Doherty et al. |
| 2010/0104470 A1 | 4/2010 | McCabe |
| 2010/0177076 A1 | 7/2010 | Essinger et al. |
| 2010/0177080 A1 | 7/2010 | Essinger et al. |
| 2010/0177707 A1 | 7/2010 | Essinger et al. |
| 2010/0177749 A1 | 7/2010 | Essinger et al. |
| 2011/0169999 A1 | 7/2011 | Grunow et al. |
| 2011/0202554 A1 | 8/2011 | Powilleit et al. |
| 2012/0111946 A1 | 5/2012 | Golant |
| 2012/0168512 A1 | 7/2012 | Kotlarsky et al. |
| 2012/0193423 A1 | 8/2012 | Samek |
| 2012/0203647 A1 | 8/2012 | Smith |
| 2012/0223141 A1 | 9/2012 | Good et al. |
| 2013/0043312 A1 | 2/2013 | Van Horn |
| 2013/0045132 A1 | 2/2013 | Tumanov |
| 2013/0075168 A1 | 3/2013 | Amundsen et al. |
| 2013/0175341 A1 | 7/2013 | Kearney et al. |
| 2013/0175343 A1 | 7/2013 | Good |
| 2013/0257744 A1 | 10/2013 | Daghigh et al. |
| 2013/0257759 A1 | 10/2013 | Daghigh |
| 2013/0270346 A1 | 10/2013 | Xian et al. |
| 2013/0287258 A1 | 10/2013 | Kearney |
| 2013/0292475 A1 | 11/2013 | Kotlarsky et al. |
| 2013/0292477 A1 | 11/2013 | Hennick et al. |
| 2013/0293539 A1 | 11/2013 | Hunt et al. |
| 2013/0293540 A1 | 11/2013 | Laffargue et al. |
| 2013/0306728 A1 | 11/2013 | Thuries et al. |
| 2013/0306731 A1 | 11/2013 | Pedraro |
| 2013/0307964 A1 | 11/2013 | Bremer et al. |
| 2013/0308625 A1 | 11/2013 | Park et al. |
| 2013/0313324 A1 | 11/2013 | Koziol et al. |
| 2013/0313325 A1 | 11/2013 | Wilz et al. |
| 2013/0342717 A1 | 12/2013 | Havens et al. |
| 2014/0001267 A1 | 1/2014 | Giordano et al. |
| 2014/0002828 A1 | 1/2014 | Laffargue et al. |
| 2014/0008439 A1 | 1/2014 | Wang |
| 2014/0025584 A1 | 1/2014 | Liu et al. |
| 2014/0100813 A1 | 1/2014 | Showering |
| 2014/0034734 A1 | 2/2014 | Sauerwein |
| 2014/0036848 A1 | 2/2014 | Pease et al. |
| 2014/0039693 A1 | 2/2014 | Havens et al. |
| 2014/0042814 A1 | 2/2014 | Kather et al. |
| 2014/0049120 A1 | 2/2014 | Kohtz et al. |
| 2014/0049635 A1 | 2/2014 | Laffargue et al. |
| 2014/0061306 A1 | 3/2014 | Wu et al. |
| 2014/0063289 A1 | 3/2014 | Hussey et al. |
| 2014/0066136 A1 | 3/2014 | Sauerwein et al. |
| 2014/0067692 A1 | 3/2014 | Ye et al. |
| 2014/0070005 A1 | 3/2014 | Nahill et al. |
| 2014/0071840 A1 | 3/2014 | Venancio |
| 2014/0074746 A1 | 3/2014 | Wang |
| 2014/0076974 A1 | 3/2014 | Havens et al. |
| 2014/0078341 A1 | 3/2014 | Havens et al. |
| 2014/0078342 A1 | 3/2014 | Li et al. |
| 2014/0078345 A1 | 3/2014 | Showering |
| 2014/0098792 A1 | 4/2014 | Wang et al. |
| 2014/0100774 A1 | 4/2014 | Showering |
| 2014/0103115 A1 | 4/2014 | Meier et al. |
| 2014/0104413 A1 | 4/2014 | McCloskey et al. |
| 2014/0104414 A1 | 4/2014 | McCloskey et al. |
| 2014/0104416 A1 | 4/2014 | Giordano et al. |
| 2014/0104451 A1 | 4/2014 | Todeschini et al. |
| 2014/0106594 A1 | 4/2014 | Skvoretz |
| 2014/0106725 A1 | 4/2014 | Sauerwein |
| 2014/0108010 A1 | 4/2014 | Maltseff et al. |
| 2014/0108402 A1 | 4/2014 | Gomez et al. |
| 2014/0108682 A1 | 4/2014 | Caballero |
| 2014/0110485 A1 | 4/2014 | Toa et al. |
| 2014/0114530 A1 | 4/2014 | Fitch et al. |
| 2014/0124577 A1 | 5/2014 | Wang et al. |
| 2014/0124579 A1 | 5/2014 | Ding |
| 2014/0125842 A1 | 5/2014 | Winegar |
| 2014/0125853 A1 | 5/2014 | Wang |
| 2014/0125999 A1 | 5/2014 | Longacre et al. |
| 2014/0129378 A1 | 5/2014 | Richardson |
| 2014/0131438 A1 | 5/2014 | Kearney |

(56) References Cited

U.S. PATENT DOCUMENTS

| | | |
|---|---|---|
| 2014/0131441 A1 | 5/2014 | Nahill et al. |
| 2014/0131443 A1 | 5/2014 | Smith |
| 2014/0131444 A1 | 5/2014 | Wang |
| 2014/0131445 A1 | 5/2014 | Ding et al. |
| 2014/0131448 A1 | 5/2014 | Xian et al. |
| 2014/0133379 A1 | 5/2014 | Wang et al. |
| 2014/0136208 A1 | 5/2014 | Maltseff et al. |
| 2014/0140585 A1 | 5/2014 | Wang |
| 2014/0151453 A1 | 6/2014 | Meier et al. |
| 2014/0152882 A1 | 6/2014 | Samek et al. |
| 2014/0158770 A1 | 6/2014 | Sevier et al. |
| 2014/0159869 A1 | 6/2014 | Zumsteg et al. |
| 2014/0166755 A1 | 6/2014 | Liu et al. |
| 2014/0166757 A1 | 6/2014 | Smith |
| 2014/0166759 A1 | 6/2014 | Liu et al. |
| 2014/0168787 A1 | 6/2014 | Wang et al. |
| 2014/0175165 A1 | 6/2014 | Havens et al. |
| 2014/0175172 A1 | 6/2014 | Jovanovski et al. |
| 2014/0191644 A1 | 7/2014 | Chaney |
| 2014/0191913 A1 | 7/2014 | Ge et al. |
| 2014/0197238 A1 | 7/2014 | Lui et al. |
| 2014/0197239 A1 | 7/2014 | Havens et al. |
| 2014/0197304 A1 | 7/2014 | Feng et al. |
| 2014/0203087 A1 | 7/2014 | Smith et al. |
| 2014/0204268 A1 | 7/2014 | Grunow et al. |
| 2014/0214631 A1 | 7/2014 | Hansen |
| 2014/0217166 A1 | 8/2014 | Berthiaume et al. |
| 2014/0217180 A1 | 8/2014 | Liu |
| 2014/0231500 A1 | 8/2014 | Ehrhart et al. |
| 2014/0232930 A1 | 8/2014 | Anderson |
| 2014/0247315 A1 | 9/2014 | Marty et al. |
| 2014/0263493 A1 | 9/2014 | Amurgis et al. |
| 2014/0263645 A1 | 9/2014 | Smith et al. |
| 2014/0270196 A1 | 9/2014 | Braho et al. |
| 2014/0270229 A1 | 9/2014 | Braho |
| 2014/0278387 A1 | 9/2014 | DiGregorio |
| 2014/0282210 A1 | 9/2014 | Bianconi |
| 2014/0284384 A1 | 9/2014 | Lu et al. |
| 2014/0288933 A1 | 9/2014 | Braho et al. |
| 2014/0297058 A1 | 10/2014 | Barker et al. |
| 2014/0299665 A1 | 10/2014 | Barber et al. |
| 2014/0312121 A1 | 10/2014 | Lu et al. |
| 2014/0319220 A1 | 10/2014 | Coyle |
| 2014/0319221 A1 | 10/2014 | Oberpriller et al. |
| 2014/0326787 A1 | 11/2014 | Barten |
| 2014/0332590 A1 | 11/2014 | Wang et al. |
| 2014/0344943 A1 | 11/2014 | Todeschini et al. |
| 2014/0346233 A1 | 11/2014 | Liu et al. |
| 2014/0351317 A1 | 11/2014 | Smith et al. |
| 2014/0353373 A1 | 12/2014 | Van Horn et al. |
| 2014/0361073 A1 | 12/2014 | Qu et al. |
| 2014/0361082 A1 | 12/2014 | Xian et al. |
| 2014/0362184 A1 | 12/2014 | Jovanovski et al. |
| 2014/0363015 A1 | 12/2014 | Braho |
| 2014/0369511 A1 | 12/2014 | Sheerin et al. |
| 2014/0374483 A1 | 12/2014 | Lu |
| 2014/0374485 A1 | 12/2014 | Xian et al. |
| 2015/0001301 A1 | 1/2015 | Ouyang |
| 2015/0001304 A1 | 1/2015 | Todeschini |
| 2015/0003673 A1 | 1/2015 | Fletcher |
| 2015/0009338 A1 | 1/2015 | Laffargue et al. |
| 2015/0009610 A1 | 1/2015 | London et al. |
| 2015/0014416 A1 | 1/2015 | Kotlarsky et al. |
| 2015/0021397 A1 | 1/2015 | Rueblinger et al. |
| 2015/0028102 A1 | 1/2015 | Ren et al. |
| 2015/0028103 A1 | 1/2015 | Jiang |
| 2015/0028104 A1 | 1/2015 | Ma et al. |
| 2015/0029002 A1 | 1/2015 | Yeakley et al. |
| 2015/0032709 A1 | 1/2015 | Maloy et al. |
| 2015/0039309 A1 | 2/2015 | Braho et al. |
| 2015/0040378 A1 | 2/2015 | Saber et al. |
| 2015/0048168 A1 | 2/2015 | Fritz et al. |
| 2015/0049347 A1 | 2/2015 | Laffargue et al. |
| 2015/0051992 A1 | 2/2015 | Smith |
| 2015/0053766 A1 | 2/2015 | Havens et al. |
| 2015/0053768 A1 | 2/2015 | Wang et al. |
| 2015/0053769 A1 | 2/2015 | Thuries et al. |
| 2015/0062366 A1 | 3/2015 | Liu et al. |
| 2015/0063215 A1 | 3/2015 | Wang |
| 2015/0063676 A1 | 3/2015 | Lloyd et al. |
| 2015/0069130 A1 | 3/2015 | Gannon |
| 2015/0071819 A1 | 3/2015 | Todeschini |
| 2015/0083800 A1 | 3/2015 | Li et al. |
| 2015/0086114 A1 | 3/2015 | Todeschini |
| 2015/0088522 A1 | 3/2015 | Hendrickson et al. |
| 2015/0096872 A1 | 4/2015 | Woodburn |
| 2015/0099557 A1 | 4/2015 | Pettinelli et al. |
| 2015/0100196 A1 | 4/2015 | Hollifield |
| 2015/0102109 A1 | 4/2015 | Huck |
| 2015/0115035 A1 | 4/2015 | Meier et al. |
| 2015/0127791 A1 | 5/2015 | Kosecki et al. |
| 2015/0128116 A1 | 5/2015 | Chen et al. |
| 2015/0129659 A1 | 5/2015 | Feng et al. |
| 2015/0133047 A1 | 5/2015 | Smith et al. |
| 2015/0134470 A1 | 5/2015 | Hejl et al. |
| 2015/0136851 A1 | 5/2015 | Harding et al. |
| 2015/0136854 A1 | 5/2015 | Lu et al. |
| 2015/0142492 A1 | 5/2015 | Kumar |
| 2015/0144692 A1 | 5/2015 | Hejl |
| 2015/0144698 A1 | 5/2015 | Teng et al. |
| 2015/0144701 A1 | 5/2015 | Xian et al. |
| 2015/0149946 A1 | 5/2015 | Benos et al. |
| 2015/0161429 A1 | 6/2015 | Xian |
| 2015/0169925 A1 | 6/2015 | Chang et al. |
| 2015/0169929 A1 | 6/2015 | Williams et al. |
| 2015/0186703 A1 | 7/2015 | Chen et al. |
| 2015/0193644 A1 | 7/2015 | Kearney et al. |
| 2015/0193645 A1 | 7/2015 | Colavito et al. |
| 2015/0199957 A1 | 7/2015 | Funyak et al. |
| 2015/0204671 A1 | 7/2015 | Showering |
| 2015/0210199 A1 | 7/2015 | Payne |
| 2015/0220753 A1 | 8/2015 | Zhu et al. |
| 2015/0254485 A1 | 9/2015 | Feng et al. |
| 2015/0327012 A1 | 11/2015 | Bian et al. |
| 2016/0014251 A1 | 1/2016 | Hejl |
| 2016/0040982 A1 | 2/2016 | Li et al. |
| 2016/0042241 A1 | 2/2016 | Todeschini |
| 2016/0057230 A1 | 2/2016 | Todeschini et al. |
| 2016/0109219 A1 | 4/2016 | Ackley et al. |
| 2016/0109220 A1 | 4/2016 | Laffargue |
| 2016/0109224 A1 | 4/2016 | Thuries et al. |
| 2016/0112631 A1 | 4/2016 | Ackley et al. |
| 2016/0112643 A1 | 4/2016 | Laffargue et al. |
| 2016/0124516 A1 | 5/2016 | Schoon et al. |
| 2016/0125217 A1 | 5/2016 | Todeschini |
| 2016/0125342 A1 | 5/2016 | Miller et al. |
| 2016/0133253 A1 | 5/2016 | Braho et al. |
| 2016/0171720 A1 | 6/2016 | Todeschini |
| 2016/0178479 A1 | 6/2016 | Goldsmith |
| 2016/0180678 A1 | 6/2016 | Ackley et al. |
| 2016/0189087 A1 | 6/2016 | Morton et al. |
| 2016/0125873 A1 | 7/2016 | Braho et al. |
| 2016/0227912 A1 | 8/2016 | Oberpriller et al. |
| 2016/0232891 A1 | 8/2016 | Pecorari |
| 2016/0292477 A1 | 10/2016 | Bidwell |
| 2016/0294779 A1 | 10/2016 | Yeakley et al. |
| 2016/0306769 A1 | 10/2016 | Kohtz et al. |
| 2016/0314276 A1 | 10/2016 | Sewell et al. |
| 2016/0314294 A1 | 10/2016 | Kubler et al. |

FOREIGN PATENT DOCUMENTS

| | | |
|---|---|---|
| WO | 2014019130 A1 | 2/2014 |
| WO | 2014110495 A1 | 7/2014 |

OTHER PUBLICATIONS

U.S. Appl. No. 14/277,337 for Multipurpose Optical Reader, filed May 14, 2014 (Jovanovski et al.); 59 pages; now abandoned.

U.S. Appl. No. 14/446,391 for Multifunction Point of Sale Apparatus With Optical Signature Capture filed Jul. 30, 2014 (Good et al.); 37 pages; now abandoned.

(56) References Cited

OTHER PUBLICATIONS

U.S. Appl. No. 29/516,892 for Table Computer filed Feb. 6, 2015 (Bidwell et al.); 13 pages.
U.S. Appl. No. 29/523,098 for Handle for a Tablet Computer filed Apr. 7, 2015 (Bidwell et al.); 17 pages.
U.S. Appl. No. 29/528,890 for Mobile Computer Housing filed Jun. 2, 2015 (Fitch et al.); 61 pages.
U.S. Appl. No. 29/526,918 for Charging Base filed May 14, 2015 (Fitch et al.); 10 pages.
U.S. Appl. No. 14/715,916 for Evaluating Image Values filed May 19, 2015 (Ackley); 60 pages.
U.S. Appl. No. 29/525,068 for Tablet Computer With Removable Scanning Device filed Apr. 27, 2015 (Schulte et al.); 19 pages.
U.S. Appl. No. 29/468,118 for an Electronic Device Case, filed Sep. 26, 2013 (Oberpriller et al.); 44 pages.
U.S. Appl. No. 29/530,600 for Cyclone filed Jun. 18, 2015 (Vargo et al); 16 pages.
U.S. Appl. No. 14/707,123 for Application Independent DEX/UCS Interface filed May 8, 2015 (Pape); 47 pages.
U.S. Appl. No. 14/283,282 for Terminal Having Illumination and Focus Control filed May 21, 2014 (Liu et al.); 31 pages; now abandoned.
U.S. Appl. No. 14/705,407 for Method and System to Protect Software-Based Network-Connected Devices From Advanced Persistent Threat filed May 6, 2015 (Hussey et al.); 42 pages.
U.S. Appl. No. 14/704,050 for Intermediate Linear Positioning filed May 5, 2015 (Charpentier et al.); 60 pages.
U.S. Appl. No. 14/705,012 for Hands-Free Human Machine Interface Responsive to a Driver of a Vehicle filed May 6, 2015 (Fitch et al.); 44 pages.
U.S. Appl. No. 14/715,672 for Augumented Reality Enabled Hazard Display filed May 19, 2015 (Venkatesha et al.); 35 pages.
U.S. Appl. No. 14/735,717 for Indicia-Reading Systems Having an Interface With a User's Nervous System filed Jun. 10, 2015 (Todeschini); 39 pages.
U.S. Appl. No. 14/702,110 for System and Method for Regulating Barcode Data Injection Into a Running Application on a Smart Device filed May 1, 2015 (Todeschini et al.); 38 pages.
U.S. Appl. No. 14/747,197 for Optical Pattern Projector filed Jun. 23, 2015 (Thuries et al.); 33 pages.
U.S. Appl. No. 14/702,979 for Tracking Battery Conditions filed May 4, 2015 (Young et al.); 70 pages.
U.S. Appl. No. 29/529,441 for Indicia Reading Device filed Jun. 8, 2015 (Zhou et al.); 14 pages.
U.S. Appl. No. 14/747,490 for Dual-Projector Three-Dimensional Scanner filed Jun. 23, 2015 (Jovanovski et al.); 40 pages.
U.S. Appl. No. 14/740,320 for Tactile Switch for a Mobile Electronic Device filed Jun. 16, 2015 (Barndringa); 38 pages.
U.S. Appl. No. 14/740,373 for Calibrating a Volume Dimensioner filed Jun. 16, 2015 (Ackley et al.); 63 pages.

FIG. 3

DEVICE HAVING LIGHT SOURCE TO REDUCE SURFACE PATHOGENS

CROSS-REFERENCE TO RELATED APPLICATION

The present application claims the benefit of U.S. patent application Ser. No. 14/019,616 for a Device Having Light Source to Reduce Surface Pathogens filed Sep. 6, 2013 (and published Mar. 12, 2015 as U.S. Patent Publication No. 2015/0071819), now U.S. Pat. No. 9,572,901. Each of the foregoing patent application, patent publication, and patent is hereby incorporated by reference in its entirety.

FIELD OF THE INVENTION

The present invention relates to the field of decontamination and, more specifically, to a self-disinfecting device.

BACKGROUND

Many products are used in environments where bacteria reduction or disinfection is mission critical. As an example, products such as hand-held mobile computers and bar code scanners are used regularly in hospitals, where decontamination is critically important.

In the hospital environment, hand-held mobile computers and bar code scanners are carried room-to-room by doctors and nurses in the performance of their duties. Because these devices may be regularly used or carried by doctors, nurses, or other hospital staff throughout the hospital environment, these devices acquire and carry with them contaminants and pathogens, such as bacteria.

As devices such as hand-held mobile computers and bar code scanners are carried throughout the hospital environment and from room to room, patients can be exposed to contaminants (e.g., bacteria) that are carried by the devices posing serious health risks. Because of the risk to patients and visitors, as well as to hospital employees, hospital staff are required to frequently clean these kinds of devices.

While traditional methods of cleansing, such as the application and use of cleaning solutions, is a somewhat effective method of reducing bacteria or other contaminants, the effectiveness of such traditional methods of disinfection is completely dependent upon the quality and thoroughness of the cleaning job that is performed by each employee that is tasked with cleaning the devices.

Therefore, a need exists for more efficient and effective methods and devices for disinfecting products, including but not limited to hand-held mobile computers and bar code scanners.

SUMMARY

Accordingly, in one aspect, the present invention embraces self-disinfecting devices including a housing that has translucent material through which light (e.g., electromagnetic radiation) may pass, a light source positioned within the housing, and an electrical power source for powering the light source. The light source illuminates the translucent material such that the light source disinfects the surface of the housing through which the light passes.

In another exemplary embodiment, the self-disinfecting device includes a power source for powering the device's light source.

In yet another exemplary embodiment, the power source for the self-disinfecting device is an electrical power source.

In yet another exemplary embodiment, the self-disinfecting device includes a reflector that directs light produced by the light source to the housing's translucent material.

In yet another exemplary embodiment, the self-disinfecting device includes a lens to direct light produced by the device's light source to the housing's translucent material.

In yet another exemplary embodiment, the self-disinfecting device's light source(s) emits light at a wavelength and an intensity that kills bacteria without substantially harming human skin.

In yet another exemplary embodiment, the housing's translucent material is present in an area designed to be touched during operation of the device.

In yet another exemplary embodiment, the self-disinfecting device is a hand-held computer.

In yet another exemplary embodiment, the self-disinfecting device is a hand-held scanner.

In another aspect, the present invention embraces a hand-held device that is capable of self-disinfection. The hand-held device includes a processor and a housing that substantially encloses the processor. The housing is at least partially formed of a material that is translucent to light. The device also includes an ultraviolet light source positioned within the housing for emitting light at a wavelength and an intensity that kills bacteria on the outer surface of the housing's translucent material.

In another exemplary embodiment, the hand-held device includes a power source for powering the ultraviolet light source.

In yet another exemplary embodiment, the power source for the hand-held device is an electrical power source.

In yet another exemplary embodiment, the ultraviolet light source of the hand-held device is a light-emitting diode.

In yet another exemplary embodiment, the ultraviolet light source of the hand-held device is a plurality of light-emitting diodes arranged in an array.

In yet another exemplary embodiment, the ultraviolet light is guided to the outer surface of the housing's translucent material.

In yet another exemplary embodiment, the ultraviolet light is guided through glass to the outer surface of the housing's translucent material.

In yet another exemplary embodiment, the housing includes a handle formed of material that is translucent to ultraviolet light.

In yet another exemplary embodiment, the device is a hand-held computer.

In yet another exemplary embodiment, the device is a hand-held scanner.

In another aspect, the present invention embraces a method for disinfecting a device. The method includes providing a device that includes a processor and a light source positioned within a housing. At least a portion of the housing is translucent to radiation. The method further includes emitting radiation from the light source at a wavelength and an intensity that kills bacteria on the outer surface of the housing.

The foregoing illustrative summary, as well as other exemplary objectives and/or advantages of the invention, and the manner in which the same are accomplished, are further explained within the following detailed description and its accompanying drawings.

DETAILED DESCRIPTION

The present invention embraces self-disinfecting devices and related methods for disinfecting devices. In particular, the present invention embraces self-disinfecting devices having a housing with translucent material and an internal and/or external light source that is used to reduce surface bacteria on the translucent material. Although surface bacteria are the contaminant commonly referred to herein, this term is used in a general sense and can include any other disease causing organism or pathogen.

Non-limiting examples of typical self-disinfecting devices may include hand-held computers, hand-held scanners, and similar products that may be used in any environment where reduction of contaminants is advantageous (e.g., a hospital environment). References herein to particular kinds of devices or device environments are not intended to limit the disclosure to particular devices, and those having ordinary skill in the art will recognize that a number of products for which elimination of surface pathogens would be beneficial could be employed.

Figure 1:
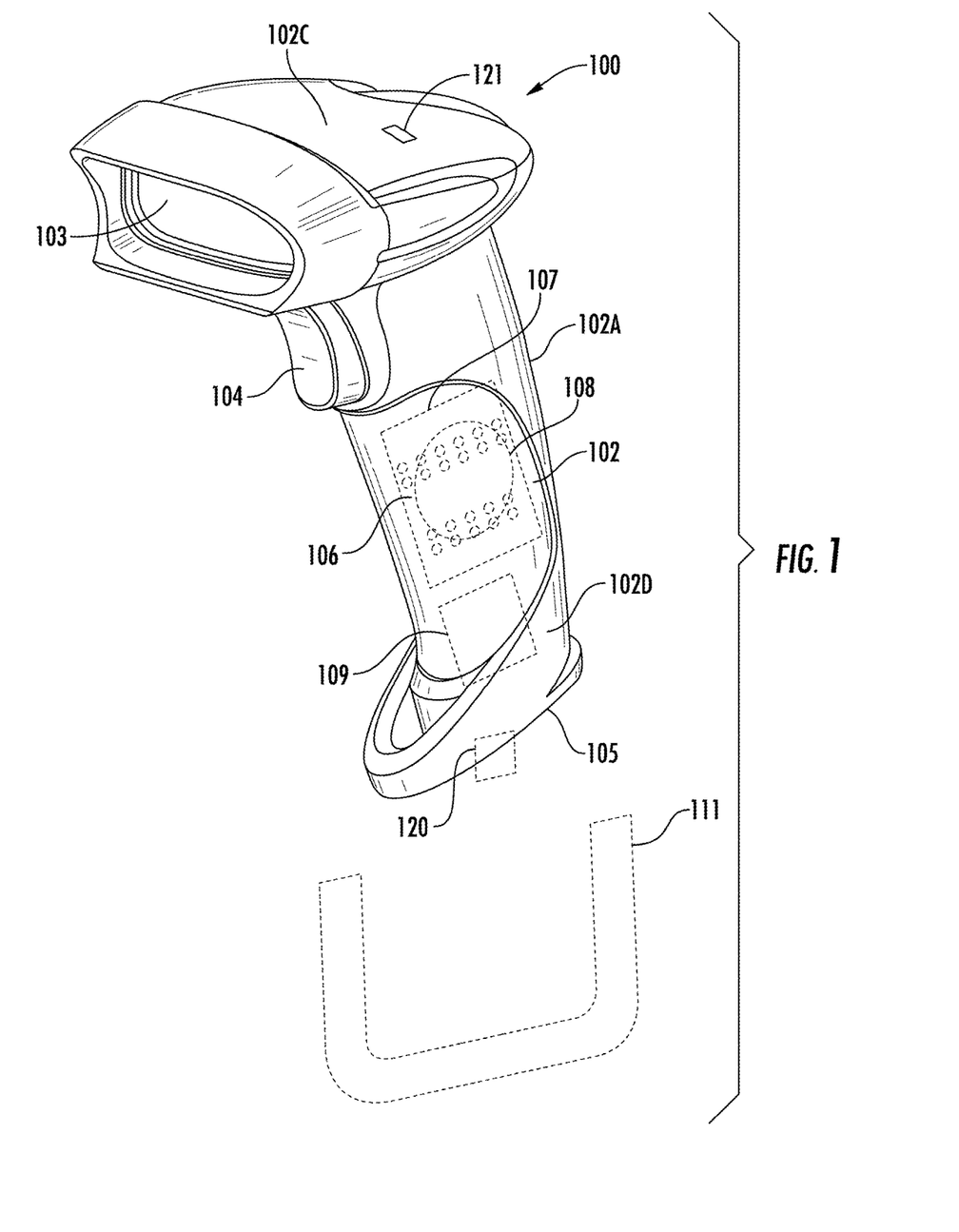
FIG. 1 depicts an exemplary self-disinfecting device and illustrates certain components for an exemplary self-disinfecting device according to the present invention.

Referring now to the drawings, FIG. 1 depicts an exemplary self-disinfecting device according to the present invention, specifically a self-disinfecting hand-held scanner (100). The exemplary self-disinfecting hand-held scanner (100) includes a hand-supportable housing (102) incorporating translucent material (102A). The translucent material (102A) may include any material that at least partially allows ultraviolet radiation to pass through to the outer surface of the translucent material (102A) at a wavelength and intensity necessary to disinfect the surface of the translucent material (102A) (e.g., plastic, glass, acrylic, resin or any other translucent material that could be used for a product housing). The translucent material (102A) may be of a kind and configuration known within the art that will not substantially degrade upon repeated or prolonged exposure to ultraviolet radiation.

As depicted in FIG. 1, the exemplary hand-held scanner's (100) housing (102) has a head portion (102C) that is provided with a light transmission window (103) integrated within the head portion of the housing (102). The light transmission window (103) may include a laser (e.g., infrared) or an image reading sensor that is utilized for reading symbols, images, and the like. As illustrated in FIG. 1, a manually actuated trigger switch (104) may be depressed to activate the scanning module.

The base structure (102D) of the hand-held scanner's housing (102) may include a charging mechanism (105) for providing electrical power from a charging base (111) to an electrical power source (109), such as an internal battery positioned within the housing (102). Alternatively, those having skill in the art will recognize that other internal or external power sources may be utilized in order to provide power to the self-disinfecting hand-held scanner (100) of the exemplary embodiment.

An ultraviolet light source (106) is positioned within the housing (102). The ultraviolet light source (106) may include one or more light-emitting-diodes (LED) (e.g., two or more LEDs configured in an LED array) or may take any other form that is capable of providing ultraviolet radiation of a sufficient wavelength and intensity known within the art to decontaminate the surface of the translucent material (102A). Although ultraviolet light and light sources are typically referred to herein, these terms are used in a general sense and can include any other light source which can be utilized to decontaminate the surface of the translucent material (102A). For example, the light source (106) may alternatively utilize HINS (High Intensity, Narrow Spectrum) light to decontaminate the surface (102A).

Reflective material (107) and/or a lens (108) may be utilized for efficiently guiding ultraviolet light from the ultraviolet light source (106) to the translucent material (102A). The ultraviolet light source (106) may alternatively be guided to the surface via total internal reflection through a medium (e.g., glass, plastic, or acrylic). A manual switch (121) may be provided on the hand-held scanner's (100) housing (102) to manually start and stop the emission of ultraviolet light from the ultraviolet light source (106) (i.e., starting and stopping the cleaning mode of the self-disinfecting hand-supportable scanner (100)).

Although internal light source (106) is depicted in FIG. 1, an at least partially external light source (not depicted) may be utilized in addition to, or as an alternative to, internal light source (106) in order to disinfect the exemplary device (100). The external light source may be positioned on the head portion (102C) above the trigger (104) of the device (100) such that the external light source is capable of disinfecting the surface of the trigger (104) and the handle portion of the housing (102) when activated. Those having skill in the art will appreciate that the external light source may alternatively be located in the charging base (111) or in other locations such that the surface of the housing (102) will be disinfected when the external light source is activated.

Figure 2:
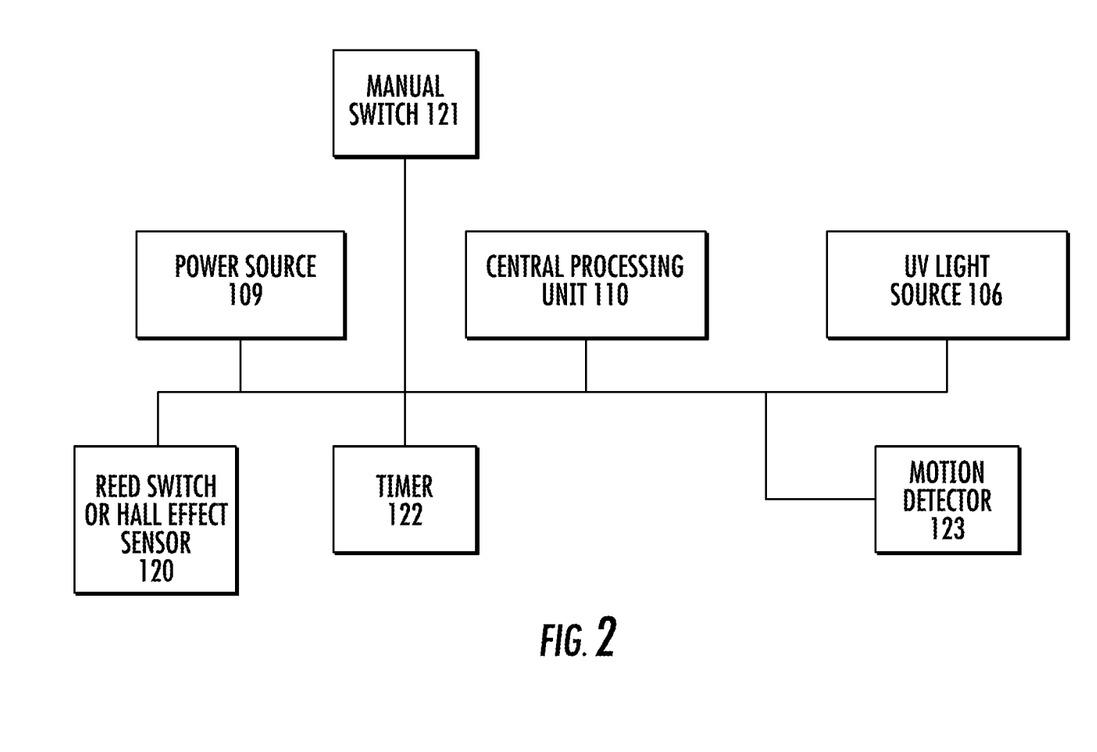
FIG. 2 illustrates via a schematic block diagram typical components for an exemplary self-disinfecting device according to the present invention.

In addition to, or in the place of, the operation of the manual switch (121), various cleaning cycles may be utilized to disinfect the exemplary device (100). In this regard, FIG. 2 is a schematic block diagram illustrating various components that may be utilized in order to implement alternative disinfecting cycles for the exemplary self-disinfecting device (100). These components may be controlled by a central processing unit (110), as well as by additional components of typical computer systems that are known in the art but are not depicted herein (e.g., a mass storage device for storing an operating system and application programs).

As depicted in FIG. 2, a timer (122) may be utilized for starting and stopping the cleaning mode at specified time periods sufficient to continually keep the device (100) at an effective level of disinfection for the environment in which it is being used. The timer may be set to disinfect the device during periods when the exemplary device (100) is not typically in use (e.g., when the device is resting in a charging base).

An exemplary self-disinfecting device (100) according to the present invention may also incorporate sensors (FIG. 2) to facilitate implementation of the disinfecting process, such as a reed switch or Hall-effect sensor (120) in the base structure (102D) and/or a motion sensor(s) (123) to detect movement of the device (100). The motion sensor (123) could be an accelerometer or some other device to sense motion that is known within the art. The motion sensor (123) could be used to prevent the discharge of ultraviolet light when the scanner (100) is being carried by a user or when the device is in use.

A Reed switch or Hall-effect sensor (120), which is positioned in the base structure (102D), may be utilized to allow the scanner (100) to enter cleaning mode when the device is on the charging base. In this regard, the device will not be carried or otherwise in use during operation of the cleaning mode. The charging base (111) could contain a magnet so that when sensor (120) was in proximity of the magnetic field, the ultraviolet "light wash" cycle would begin.

Alternatively, or in addition to implementation of the sensors (120, 123) set forth previously, light wavelengths that are not damaging to human skin may be used in connection with the cleaning cycle of the exemplary device (100). Methods of decontamination have been developed, for example, at the University of Glasgow, Scotland UK, which utilize a narrow spectrum of visible light wavelengths known as HINS (High Intensity, Narrow Spectrum) light. HINS light excites molecules within bacteria such that the bacteria produce a chemically lethal response. The HINS light, however, is not damaging to humans. To remedy concerns regarding user exposure to harmful ultraviolet radiation, this technology may also be implemented within the exemplary device (100) as a safety precaution.

Figure 3:
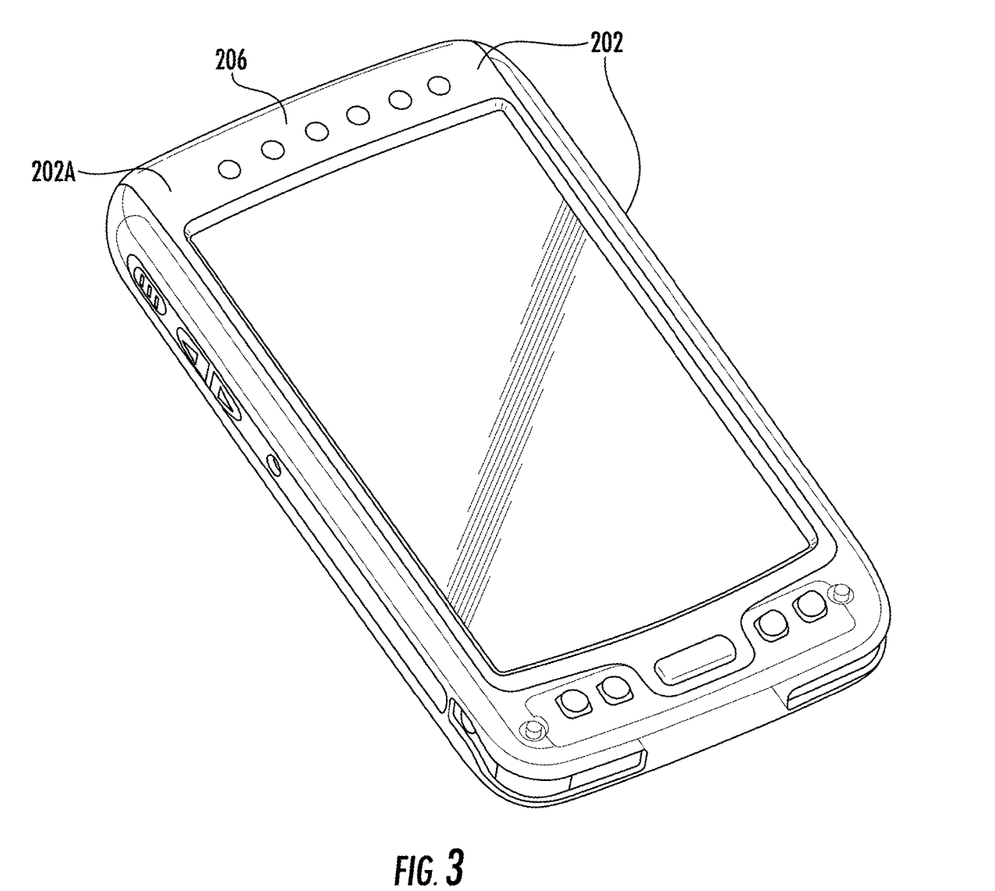
FIG. 3 depicts another exemplary self-disinfecting device and illustrates certain components for an exemplary self-disinfecting device according to the present invention.

FIG. 3 depicts an exemplary self-disinfecting hand-held computer (200) according to the present invention. The exemplary self-disinfecting hand-held computer (200) may include similar components as set forth relating to the exemplary self-disinfecting scanner (100) (FIGS. 1, 2), which are not repeated herein (FIG. 3).

As depicted (FIG. 3), the exemplary self-disinfecting hand-held computer (200) includes a hand-supportable housing (202) incorporating translucent material (202A). An ultraviolet light source (206), in this case a light-emitting-diode (LED) array, is positioned within the hand-supportable housing (202). When activated, the ultraviolet light source (206) provides ultraviolet radiation of a sufficient wavelength and intensity known within the art to decontaminate the surface of the translucent material (202A).

To supplement the present disclosure, this application incorporates entirely by reference the following patents, patent application publications, and patent applications: U.S. Pat. No. 6,832,725; U.S. Pat. No. 7,159,783; U.S. Pat. No. 7,128,266; U.S. Pat. No. 7,413,127; U.S. Pat. No. 7,726,575; U.S. Pat. No. 8,390,909; U.S. Pat. No. 8,294,969; U.S. Pat. No. 8,408,469; U.S. Pat. No. 8,408,468; U.S. Pat. No. 8,381,979; U.S. Pat. No. 8,408,464; U.S. Pat. No. 8,317,105; U.S. Pat. No. 8,366,005; U.S. Pat. No. 8,424,768; U.S. Pat. No. 8,322,622; U.S. Pat. No. 8,371,507; U.S. Pat. No. 8,376,233; U.S. Pat. No. 8,457,013; U.S. Pat. No. 8,448,863; U.S. Pat. No. 8,459,557; U.S. Pat. No. 8,469,272; U.S. Pat. No. 8,474,712; U.S. Pat. No. 8,479,992; U.S. Pat. No. 8,490,877; U.S. Pat. No. 8,517,271; U.S. Pat. No. 8,523,076; U.S. Pat. No. 8,528,819; U.S. Patent Application Publication No. 2012/0111946; U.S. Patent Application Publication No. 2012/0223141; U.S. Patent Application Publication No. 2012/0193423; U.S. Patent Application Publication No. 2012/0203647; U.S. Patent Application Publication No. 2012/0248188; U.S. Patent Application Publication No. 2012/0228382; U.S. Patent Application Publication No. 2012/0193407; U.S. Patent Application Publication No. 2012/0168511; U.S. Patent Application Publication No. 2012/0168512; U.S. Patent Application Publication No. 2010/0177749; U.S. Patent Application Publication No. 2010/0177080; U.S. Patent Application Publication No. 2010/0177707; U.S. Patent Application Publication No. 2010/0177076; U.S. Patent Application Publication No. 2009/0134221; U.S. Patent Application Publication No. 2012/0318869; U.S. Patent Application Publication No. 2013/0043312; U.S. Patent Application Publication No. 2013/0068840; U.S. Patent Application Publication No. 2013/0070322; U.S. Patent Application Publication No. 2013/0075168; U.S. Patent Application Publication No. 2013/0056285; U.S. Patent Application Publication No. 2013/0075464; U.S. Patent Application Publication No. 2013/0082104; U.S. Patent Application Publication No. 2010/0225757; U.S. Patent Application Publication No. 2013/0175343; U.S. patent application Ser. No. 13/347,193 for a HYBRID-TYPE BIOPTICAL LASER SCANNING AND DIGITAL IMAGING SYSTEM EMPLOYING DIGITAL IMAGER WITH FIELD OF VIEW OVERLAPPING FIELD OF FIELD OF LASER SCANNING SUBSYSTEM, filed Jan. 10, 2012 (Kearney et al.); U.S. patent application Ser. No. 13/367,047 for LASER SCANNING MODULES EMBODYING SILICONE SCAN ELEMENT WITH TORSIONAL HINGES, filed Feb. 6, 2012 (Feng et al.); U.S. patent application Ser. No. 13/400,748 for a LASER SCANNING BAR CODE SYMBOL READING SYSTEM HAVING INTELLIGENT SCAN SWEEP ANGLE ADJUSTMENT CAPABILITIES OVER THE WORKING RANGE OF THE SYSTEM FOR OPTIMIZED BAR CODE SYMBOL READING PERFORMANCE, filed Feb. 21, 2012 (Wilz); U.S. patent application Ser. No. 13/432,197 for a LASER SCANNING SYSTEM USING LASER BEAM SOURCES FOR PRODUCING LONG AND SHORT WAVELENGTHS IN COMBINATION WITH BEAM-WAIST EXTENDING OPTICS TO EXTEND THE DEPTH OF FIELD THEREOF WHILE RESOLVING HIGH RESOLUTION BAR CODE SYMBOLS HAVING MINIMUM CODE ELEMENT WIDTHS, filed Mar. 28, 2012 (Havens et al.); U.S. patent application Ser. No. 13/492,883 for a LASER SCANNING MODULE WITH ROTATABLY ADJUSTABLE LASER SCANNING ASSEMBLY, filed Jun. 10, 2012 (Hennick et al.); U.S. patent application Ser. No. 13/367,978 for a LASER SCANNING MODULE EMPLOYING AN ELASTOMERIC U-HINGE BASED LASER SCANNING ASSEMBLY, filed Feb. 7, 2012 (Feng et al.); U.S. patent application Ser. No. 13/852,097 for a System and Method for Capturing and Preserving Vehicle Event Data, filed Mar. 28, 2013 (Barker et al.); U.S. patent application Ser. No. 13/780,356 for a Mobile Device Having Object-Identification Interface, filed Feb. 28, 2013 (Samek et al.); U.S. patent application Ser. No. 13/780,158 for a Distraction Avoidance System, filed Feb. 28, 2013 (Sauerwein); U.S. patent application Ser. No. 13/784,933 for an Integrated Dimensioning and Weighing System, filed Mar. 5, 2013 (McCloskey et al.); U.S. patent application Ser. No. 13/785,177 for a Dimensioning System, filed Mar. 5, 2013 (McCloskey et al.); U.S. patent application Ser. No. 13/780,196 for Android Bound Service Camera Initialization, filed Feb. 28, 2013 (Todeschini et al.); U.S. patent application Ser. No. 13/792,322 for a Replaceable Connector, filed Mar. 11, 2013 (Skvoretz); U.S. patent application Ser. No. 13/780,271 for a Vehicle Computer System with Transparent Display, filed Feb. 28, 2013 (Fitch et al.); U.S. patent application Ser. No. 13/736,139 for an Electronic Device Enclosure, filed Jan. 8, 2013 (Chaney); U.S. patent application Ser. No. 13/771,508 for an Optical Redirection Adapter, filed Feb. 20, 2013 (Anderson); U.S. patent application Ser. No. 13/750,304 for Measuring Object Dimensions Using Mobile Computer, filed Jan. 25, 2013; U.S. patent application Ser. No. 13/471,973 for Terminals and Methods for Dimensioning Objects, filed May 15, 2012; U.S. patent application Ser. No. 13/895,846 for a Method of Programming a Symbol Reading System, filed Apr. 10, 2013 (Corcoran); U.S. patent application Ser. No. 13/867,386 for a Point of Sale (POS) Based Checkout System Supporting a Customer-Transparent Two-Factor Authentication Process During Product Checkout Operations, filed Apr. 22, 2013 (Cunningham et al.); U.S. patent application Ser. No. 13/888,884 for an Indicia Reading System Employing Digital Gain Control, filed May 7, 2013 (Xian et al.); U.S. patent application Ser. No. 13/895,616 for a Laser Scanning Code Symbol Reading System Employing Multi-Channel Scan Data Signal Processing with Synchronized Digital Gain Control (SDGC) for Full Range Scanning, filed May 16, 2013 (Xian et al.); U.S. patent application Ser. No. 13/897,512 for a Laser Scanning Code Symbol Reading System Providing Improved Control over the Length and Intensity Characteristics of a Laser Scan Line Projected Therefrom Using Laser Source Blanking Control, filed May 20, 2013 (Brady et al.); U.S. patent application Ser. No. 13/897,634 for a Laser Scanning Code Symbol Reading System Employing Programmable Decode Time-Window Filtering, filed May 20, 2013 (Wilz, Sr. et al.); U.S. patent application Ser. No. 13/902,242 for a System For Providing A Continuous Communication Link With A Symbol Reading Device, filed May 24, 2013 (Smith et al.); U.S. patent application Ser. No. 13/902,144, for a System and Method for Display of Information Using a Vehicle-Mount Computer, filed May 24, 2013 (Chamberlin); U.S. patent application Ser. No. 13/902,110 for a System and Method for Display of Information Using a Vehicle-Mount Computer, filed May 24, 2013 (Hollifield); U.S. patent application Ser. No. 13/912,262 for a Method of Error Correction for 3D Imaging Device, filed Jun. 7, 2013 (Jovanovski et al.); U.S. patent application Ser. No. 13/912,702 for a System and Method for Reading Code Symbols at Long Range Using Source Power Control, filed Jun. 7, 2013 (Xian et al.); U.S. patent application Ser. No. 13/922,339 for a System and Method for Reading Code Symbols Using a Variable Field of View, filed Jun. 20, 2013 (Xian et al.); U.S. patent application Ser. No. 13/927,398 for a Code Symbol Reading System Having Adaptive Autofocus, filed Jun. 26, 2013 (Todeschini); U.S. patent application Ser. No. 13/930,913 for a Mobile Device Having an Improved User Interface for Reading Code Symbols, filed Jun. 28, 2013 (Gelay et al.); U.S. patent application Ser. No. 13/933,415 for an Electronic Device Case, filed Jul. 2, 2013 (London et al.); U.S. patent application Ser. No. 13/947,296 for a System and Method for Selectively Reading Code Symbols, filed Jul. 22, 2013 (Rueblinger et al.); U.S. patent application Ser. No. 13/950,544 for a Code Symbol Reading System Having Adjustable Object Detection, filed Jul. 25, 2013 (Jiang); U.S. patent application Ser. No. 13/961,408 for a Method for Manufacturing Laser Scanners, filed Aug. 7, 2013 (Saber et al.); U.S. patent application Ser. No. 13/973,315 for a Symbol Reading System Having Predictive Diagnostics, filed Aug. 22, 2013 (Nahill et al.); U.S. patent application Ser. No. 13/973,354 for a Pairing Method for Wireless Scanner via RFID, filed Aug. 22, 2013 (Wu et al.); and U.S. patent application Ser. No. 13/974,374 for Authenticating Parcel Consignees with Indicia Decoding Devices, filed Aug. 23, 2013 (Ye et al.).

In the specification and/or figures, typical embodiments and environments of the invention have been disclosed. The present invention is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The invention claimed is:

1. A hand-held device, comprising:
a processor;
a laser or image sensor for reading symbology;
a housing that substantially encloses the processor and the laser or image sensor, the housing being at least partially formed of a rigid material that is translucent to radiation; and
a radiation source positioned within the housing for emitting radiation at a wavelength and an intensity that kills pathogens on the outer surface of the housing's translucent material;
wherein at least a portion of the radiation is emitted from the radiation source orthogonal to the inner surface of the translucent material and through the translucent material to kill pathogens on the outer surface of the translucent material.

2. The hand-held device according to claim 1, comprising a motion sensor for preventing the emission of radiation from the radiation source when the hand-held device is moving.

3. The hand-held device according to claim 1, comprising a timer for starting and stopping the emission of radiation from the radiation source.

4. The hand-held device according to claim 1, comprising a switch or sensor for detecting when the hand-held device is positioned in a charging base and starting and stopping the emission of radiation from the radiation source.

5. The hand-held device according to claim 1, wherein the radiation source comprises a light-emitting diode.

6. The hand-held device according to claim 1, wherein the radiation source comprises a plurality of light-emitting diodes arranged in an array.

7. The hand-held device according to claim 1, wherein the radiation is guided to the outer surface of the housing's translucent material.

8. The hand-held device according to claim 1, wherein the radiation is guided through glass to the outer surface of the housing's translucent material.

9. The hand-held device according to claim 1, wherein the housing comprises a handle formed of material that is translucent to ultraviolet light.

10. A hand-held device, comprising:
a processor, an image sensor for reading code symbology, and a radiation source positioned within a housing;
wherein a portion of the housing comprises a rigid material that is translucent to radiation;
wherein the radiation source emits radiation at a wavelength and an intensity that kills pathogens on an outer surface of the housing's translucent material;
wherein the radiation emitted from the radiation source is directed orthogonal to an inner surface of the translucent material and through the translucent material to kill pathogens on the outer surface of the housing's translucent material.

11. The hand-held device according to claim 10, comprising a motion sensor for preventing the emission of radiation from the radiation source when the hand-held device is moving.

12. The hand-held device according to claim 10, comprising a timer for starting and stopping the emission of radiation from the radiation source.

13. The hand-held device according to claim 10, comprising a switch or sensor for detecting when the hand-held device is positioned in a charging base and starting and stopping the emission of radiation from the radiation source.

14. The hand-held device according to claim 10, wherein the radiation source comprises a plurality of light emitting diodes arranged in an array.

15. The hand-held device to claim 10, wherein the radiation is guided through glass to the outer surface of the housing's translucent material.

16. A hand-held device, comprising:
an image sensor for reading symbols;
a processor;
a housing containing the image sensor and the processor, the housing including rigid material that is translucent to radiation; and
at least one radiation source positioned within the housing that, when illuminated, emits radiation at a wavelength and an intensity that kills pathogens on an outer surface of the housing's translucent material;
wherein a portion of the radiation emitted from the at least one radiation source is emitted orthogonal to an inner surface of the translucent material and through the translucent material to kill pathogens on the outer surface of the housing.

17. The hand-held device according to claim 16, comprising a motion sensor for preventing the emission of radiation from the radiation source when the hand-held device is moving.

18. The hand-held device according to claim 16, comprising a timer for starting and stopping the emission of radiation from the radiation source.

19. The hand-held device according to claim 16, comprising a switch or sensor for detecting when the hand-held device is positioned in a charging base and starting and stopping the emission of radiation from the radiation source.

20. The device according to claim 16, wherein the radiation source comprises an ultraviolet light-emitting diode.

* * * * *